United States Patent [19]

Hammond et al.

[11] Patent Number: 5,404,387

[45] Date of Patent: Apr. 4, 1995

[54] BODY SCANNING SYSTEM

[76] Inventors: David J. Hammond, 28 Wemmer Drive, Discovery, Transvaal, South Africa; Michael W. N. Singer, 5 Rye Close, Maidenhead, Berkshire SL6 3NZ, United Kingdom; Rudolf W. Glatthaar, 9 Oribi Street, Constantia Kloof Ext 9, Roodepoort, Transvaal, South Africa; Gerhard Laniewski, 6 York Street,, Helderkruin Roodepoort, Transvaal, South Africa; Sudhir N. Surujhlal, 28 Fair-Ridge, 118 4th Avenue, Fairlands, Transvaal, South Africa; Forrester D. De Beer, 2 Wright Street, Parkrand Boksburg, Transvaal, South Africa; Pieter G. Roos, 571 Honeydew Road West, Sundowner, Randburg, Transvaal, South Africa

[21] Appl. No.: 152,403

[22] Filed: Nov. 15, 1993

[30] Foreign Application Priority Data

Nov. 13, 1992 [GB] United Kingdom ................ 9223818

[51] Int. Cl.⁶ ............................................ H05G 1/42
[52] U.S. Cl. .................................... 378/98.3; 378/62; 378/147
[58] Field of Search ............... 378/99, 62, 98, 176, 378/4, 14, 145, 146, 147, 42, 98.8, 98.3, 98.6, 98.2; 358/111

[56] References Cited

U.S. PATENT DOCUMENTS

| | | | |
|---|---|---|---|
| 3,780,291 | 12/1973 | Stein et al. | 378/146 |
| 3,919,467 | 11/1975 | Peugeot | 378/98.2 |
| 4,599,740 | 7/1986 | Cable | 378/57 |
| 5,138,642 | 8/1992 | McCroskey et al. | 378/62 |
| 5,150,394 | 9/1992 | Karellas | 378/99 |
| 5,181,234 | 1/1993 | Smith | 378/87 |
| 5,187,730 | 2/1993 | Fujihara | 378/99 |

FOREIGN PATENT DOCUMENTS

| | | |
|---|---|---|
| 0168090 | 1/1986 | European Pat. Off. . |
| 0168883 | 1/1986 | European Pat. Off. . |
| 0265010 | 4/1988 | European Pat. Off. . |
| 0286393 | 10/1988 | European Pat. Off. . |
| 2320144 | 10/1973 | Germany . |
| 88/7769 | 10/1988 | South Africa . |
| 89/3364 | 5/1989 | South Africa . |
| 89/3365 | 5/1989 | South Africa . |
| 89/3366 | 5/1989 | South Africa . |
| 2176680 | 12/1986 | United Kingdom . |
| 2188508 | 9/1987 | United Kingdom . |
| WO91/11813 | 8/1991 | WIPO . |

OTHER PUBLICATIONS

Atari, "Performance characteristics of a real-time digital z-ray fluoroscopic system using an intensified charge injection device camera and CsI:Na crystal," Medical Physics, vol. 16, No. 6, pp. 862–872, Dec. 1989.

Gluer et al., "A fast low-noise line scan x-ray detector," Medical Physics, vol. 16, No. 1, pp. 98–104, Feb. 1989.

Declerck, "Solid State Imagers and Their Applications," SPIE, vol. 591, pp. 24–30, Nov. 1985.

Abstract "Diffraction tomography systems and methods," A. Devaney, EP 109341 A2, May 23, 1984.

Abstract "Method and system for dimensional and weight measurement of articles of manufacture by computer tomography," Hoffman et al., WO 89/12281 A1, Dec. 14, 1989.

Primary Examiner—David P. Porta
Assistant Examiner—Don Wong
Attorney, Agent, or Firm—Scully, Scott, Murphy & Presser

[57] ABSTRACT

The invention concerns a method and apparatus for scanning bodies, typically human bodies (12) for security or medical purposes. In the method, the body (12) is scanned with a beam (20) of X-radiation of sufficiently low intensity that no physiological damage is suffered. The X-radiation transmitted by the body (12) is then converted into an optical image. The optical image is intensified and converted into an electronic image. The electronic image is manipulated to produce a scanned image of the body or a portion of the body. The scanned image is typically a video image.

21 Claims, 2 Drawing Sheets

BODY SCANNING SYSTEM

BACKGROUND TO THE INVENTION

THIS invention relates to a system for scanning bodies.

In one application of the invention, it may be used to scan human bodies to detect the presence thereon or therein of certain articles or substances.

SUMMARY OF THE INVENTION

According to a first aspect of the invention, there is provided a method of scanning a body, possibly a human body, the method comprising the steps of scanning the body with a beam of X-radiation, converting X-radiation transmitted by the body into an optical image, intensifying the optical image, converting the optical image into an electronic image and manipulating the electronic image to produce a scanned image of the body or a portion thereof.

The intensified optical image is preferably converted to a digital electronic image using CCD array detectors operated in drift scanning mode. The scanned image which is produced by manipulation of the digital electronic image is preferably a visual image of the body or portion thereof.

In a preferred form of the method, the transmitted X-radiation is converted to an optical image by scintillator means. It is also preferred that intensification of the optical image is by means of an optical image intensifier and possibly also by one or more fibre-optic tapers used to convey the optical image.

In one embodiment, a series of first fibre-optic tapers conveys an optical image from a corresponding series of scintillators to an optical image intensifier which intensifies the optical image, and a series of second fibre-optic tapers conveys the intensified optical image to a corresponding series of CCD array detectors, operated in drift scanning mode, for conversion to an electronic image.

Preferably, an X-ray source and imaging apparatus are located in opposition to one another on opposite sides of a scanning station and are supported by a carrier which is caused to move relative to a body located at the scanning station, thereby to scan the body. In a case where the human body is scanned, a person whose body is to be scanned will stand upright at the scanning station, and the carrier is caused to move vertically relative to the body.

Alternatively, the body may be caused to move, possibly on a conveyor belt or other transportation system, relative to a stationary X-ray source and opposing imaging apparatus.

The invention also extends to apparatus for scanning a body, the apparatus comprising an X-ray source for scanning the body with a beam of X-radiation, and imaging apparatus which includes means for converting X-radiation transmitted by the body into an optical image, means for intensifying the optical image, means for converting the intensified optical image into an electronic image and means for manipulating the electronic image to produce a scanned image of the body or a portion thereof.

In a case in which the apparatus is used to scan a human body, the intensity of the X-radiation is preferably such that the dose of X-radiation absorbed by the body during the scanning procedure is below physiologically unacceptable levels. For instance, the beam of X-radiation may be one which is of sufficiently low intensity for the human body to absorb an equivalent dose of $10 \times 10^{-6}$ sievert or less.

BRIEF DESCRIPTION OF THE DRAWINGS

The invention will now be described in more detail, by way of example only, with reference to the accompanying drawings in which.

DESCRIPTION OF AN EMBODIMENT

The system described hereunder is specifically designed to scan a human body to detect the presence thereon or therein of one or more specific articles.

Figure 1:
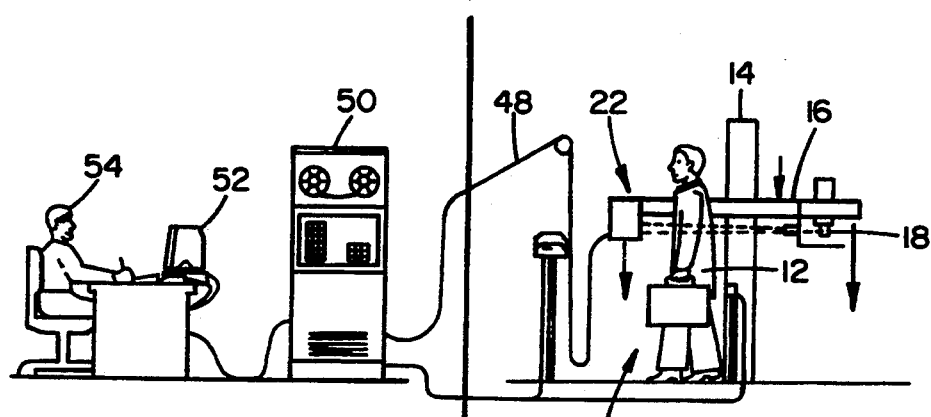
FIG. 1 illustrates a system of the invention, used to scan a human body, in a side view.

The system as depicted in FIG. 1 includes a scanning station designated with the numeral 10. Each person 12 who is to be scanned is brought to this station where, as illustrated, he stands upright during the scanning procedure. Alongside the scanning station 10 is an upright post 14 which supports a carrier 16.

A suitable vertical drive unit (not illustrated) is provided on the post 14 or on the carrier 16 to move the carrier vertically up or down the post at a predetermined, constant linear speed.

Figure 2:
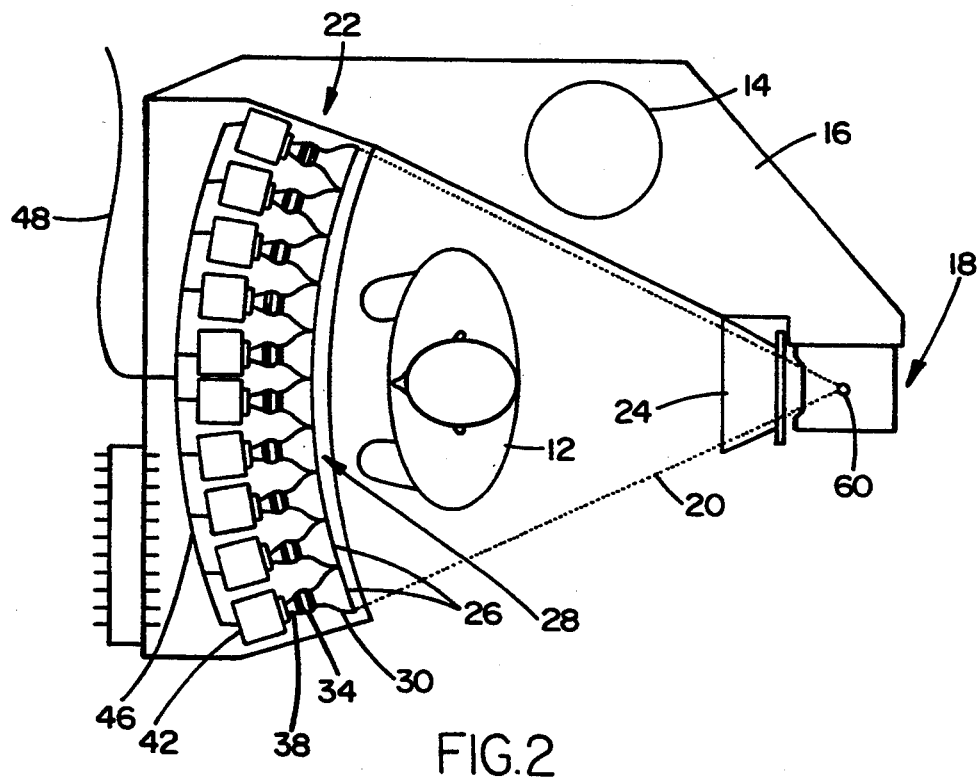
FIG. 2 shows a diagrammatic plan view of the irradiation and detection equipment used in the system of FIG. 1.

Referring also to FIG. 2, the carrier 14 incorporates an X-ray tube 18 which produces a generally horizontal, laterally fanned beam 20 of X-radiation and which directs the beam 20 through the scanning station 10 towards an arcuate detector and imaging unit 22 on the opposite side of the scanning station. It will be noted from FIG. 1 that the person 12 stands in the path of the beam 20. During scanning, the carrier is moved vertically, either up or down, so that the beam 20 traverses the full height, or a selected portion only, of the person's body.

The beam of X-radiation produced by the X-ray tube 18 is initially collimated in the vertical sense by a collimator 24 which limits the fanning of the beam 20 in a vertical plane. Having traversed the scanning zone, the beam 20 impinges on a series of laterally adjacent scintillator screens 26 which define, as illustrated, an arcuate scintillator screen array 28. As photons of X-ray energy impinge on the scintillator screens 26, the screens generate photons of light energy, in the form of an optical image, with considerable gain, i.e. many light photons are generated for each impinging X-ray photon.

In the illustrated case, where the body is scanned by an X-ray beam moving vertically relative to the body, it is important to avoid parallax effects by collimating the X-ray beam in the vertical sense to limit the vertical height of the fanned X-ray beam 20.

Figure 4:
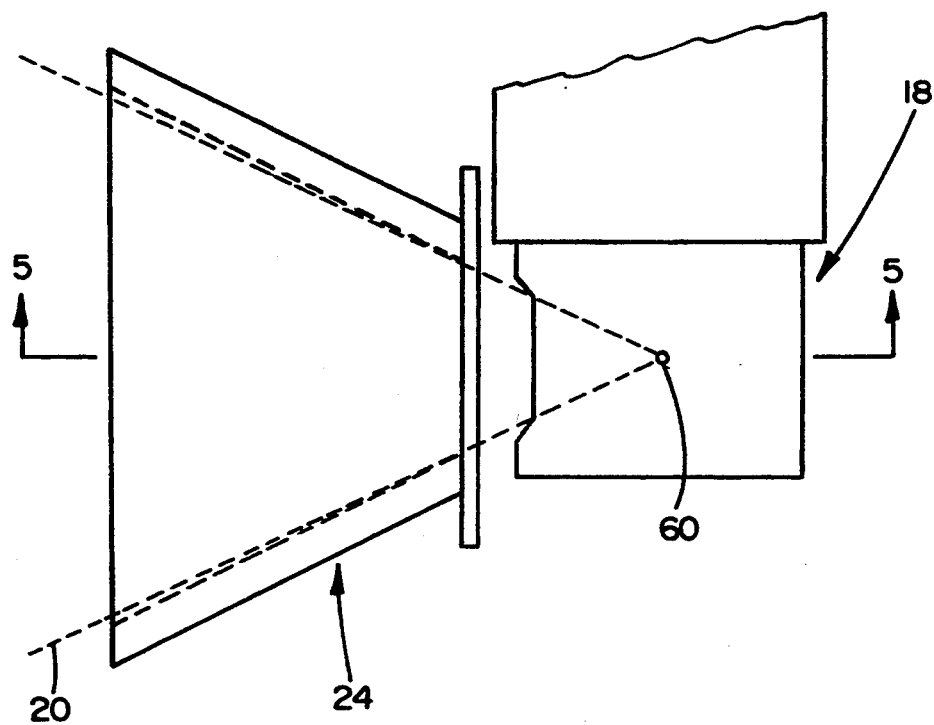
FIG. 4 shows a plan view of a preferred collimation system.
Figure 5:
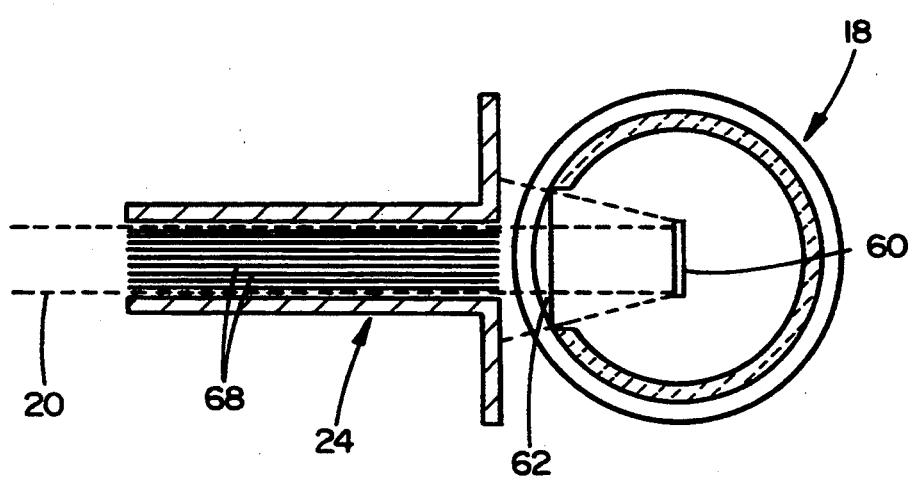
FIG. 5 shows a cross-sectional view of the preferred collimation system, at the line 5—5 in FIG. 4.

An X-ray tube and collimator system which has been found to operate satisfactorily in practice is illustrated diagrammatically in FIGS. 4 and 5 of the drawings. The preferred X-ray tube 18 is a known line focus X-ray tube. With an X-ray tube of this kind, X-rays are emitted from a source having the shape of a straight line, indicated in this case by the numeral 60. The line source 60 is orientated vertically as will be apparent from FIGS. 4 and 5, and has an emitting length corresponding to the desired height of the fanned X-ray beam 20.

As seen in FIG. 4, the divergent X-ray beam transmitted through the window 62 of the tube 18 is projected into a collimator 24 consisting of an outer housing 64 accommodating a stack 66 of closely spaced, thin, heavy metal plates 68. A collimator of this type is characterised by its grid ratio, which the ratio of the plate length in the direction of beam propagation to the clear spacing between the adjacent plates 68 in the stack. X-rays with a divergence exceeding the grid ratio impinge on the horizontal plate surfaces and are absorbed.

As will be apparent from FIG. 5, the shape of the collimator is such that lateral fanning of the beam can take place. Thus the X-ray beam 20 which finally emerge from the downstream end of the collimator 24 is a laterally fanned beam with a very low vertical divergence, determined in each case by the particular grid ratio of the collimator plate stack 66.

It will be appreciated that the intensity of the optical image which is produced is proportional to the intensity of the impinging X-radiation.

A first fibre-optic taper 30, i.e. a tapering bundle of optical fibres, is connected to each of the scintillator screens 26. Fibre-optic tapers are known to achieve good optical collection of light while maintaining good spatial resolution and low distortion of the light.

The fibre-optic taper 30 directs the optical image via a suitable coupling 32 to the input window of an image intensifier 34. It will be appreciated that the optical image presented to the input window of the image intensifier is de-magnified as a result of the shape of the fibre-optic taper. For each photon of light input to the image intensifier, the image intensifier outputs a number of light photons, via a further coupling 36, to a second fibre-optic taper 38. In other words, the image intensifier 34 intensifies the optical image presented to it by the fibre-optic taper 30.

The second fibre-optic taper 38 directs the intensified optical image, again with de-magnification, to the front face of a CCD (charge-coupled device) array detector 40 which is coupled to an electronic interface module 42.

Figure 3:
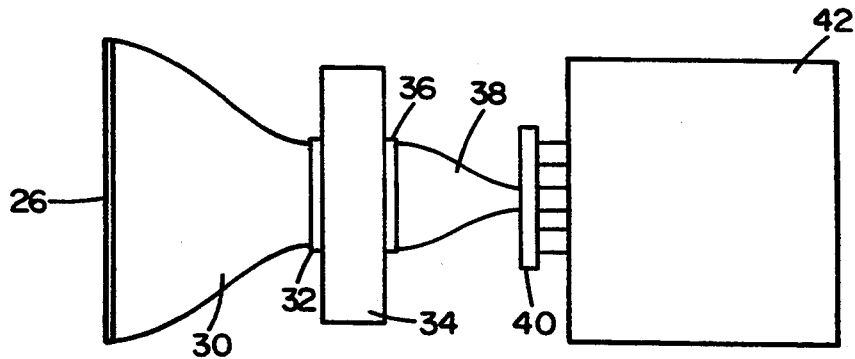
FIG. 3 diagrammatically illustrates a single detector channel of the system.

FIG. 3 of the drawings diagrammatically illustrates a single detector channel as described above.

The CCD array detectors are driven in so-called drift scanning mode. Drift scanning moves the electronic image generated at the back of the CCD array detector and continuously enhances, or updates, this image from information gathered from the optical image that "moves" concurrently across the front face of the CCD detector as the carrier 16 moves.

Since the electronic image is moved along by a constant electronic clock frequency, each point in the optical image must "move" in a straight line at a constant velocity i.e. the velocity at which the carrier 16 moves.

Those skilled in the art will recognise that the gain in image brightness effected by the image intensifier must be carefully controlled in order to avoid saturation of the CCD array detectors.

The modules 42 interface, through a databus 46 and line 48, with a processing unit 50. In the unit 50, each line of the electronic image is read out and enhanced by suitable digital electronic image processing enhancement apparatus. The unit 50 generates a video image on a monitor 52 which is viewed by an operator 54.

It will be appreciated that an important consideration in any personal X-ray scanning technique is to ensure that X-ray dose absorbed by the body does not exceed physiologically harmful levels. This is particularly so in the case of a detection system in which frequent scanning of the body is necessary. For instance, where the system is used to detect the presence of goods which may have been stolen from the workplace, scanning may take place on a daily basis, each time a person leaves the workplace.

It is anticipated that the system described above, in which X-radiation is converted to an optical image which is intensified and converted to an electronic image by a CCD array detector operated in drift scanning mode, will be able to provide the required accuracy and resolution with safe levels of initial X-ray intensity.

In practice, it is believed that in non-medical applications equivalent X-radiation dose levels of $10 \times 10^{-6}$ sievert can be sustained with adequate levels of signal resolution and accuracy.

In one application of the invention, the human body scanning system described above can be used to scan the bodies of persons with a view of detecting the presence thereon or therein of specific articles prone to theft. For instance, the bodies of persons may be scanned to detect concealed diamonds. In such a case, it is known that any diamond particles in or on the person's body will absorb a greater proportion of the incident X-radiation than the surrounding body tissue or bone. Thus the diamonds will cause relative attenuation of the X-ray signal and this will be visibly discernible in the final video image which is produced at the monitor 52. Not only will the presence of a diamond be detected, but also its location on the person's body. In such an application, the X-ray tube voltage may be selected to be in the range 150 KV to 160 KV.

Also, although specific reference has been made to the person standing during a vertical scanning procedure, it is equally possible to have the person in a prone position with horizontal scanning, or indeed to have the person moving at a constant speed, for instance on a conveyor belt, past a stationary scanning apparatus.

The detection of diamonds on the human body is but one application of the invention. In other applications, the human body could be scanned for the presence of other foreign objects, for instance pieces of metal, or for the presence of broken bones or other physiological irregularities, in a medical examination procedure.

Generally speaking the X-ray tube voltage will be chosen to suit the particular application. In medical applications such as those mentioned in the preceding paragraph, the X-ray tube voltage could, for instance, be as low as 80 KV. On the other hand, for location and analysis of heavy metals such as iron, tungsten or platinum, voltages as high as 600 KV could be employed.

The human body could also be scanned for the presence of drugs or other prohibited substances or articles such as weapons at airport security checkpoints.

The body itself is not necessarily a human body. For instance, the method and apparatus described above could be used to examine articles of luggage at airport security checkpoints.

In such cases, a version of the invention in which the body moves through the scanning station would normally be preferred to the illustrated system in which the scanning apparatus moves relative to the body.

In each application of the invention, the contrast presented on the visual image may be set at an optimum level for accurate detection of a particular article or substance by appropriate initial setting of the operating voltage and current of the X-ray tube.

It should be noted that the video or electronic images produced by the apparatus described above can, if desired, be stored in memory by the processing unit 50.

We claim:

1. A method of scanning a body, the method comprising the steps of producing a collimated beam of X-radiation by transmitting a beam of X-radiation through a collimator which includes a stack of spaced apart, parallel plates, scanning the body with the collimated beam of X-radiation by causing relative linear movement between the body and the X-ray source to take place in a direction transverse to the plates of the collimator, converting X-radiation transmitted by the body into an optical image, intensifying the optical image, converting the optical image into an electronic image and manipulating the electronic image to produce a scanned image of the body or a portion thereof.

2. A method according to claim 1 wherein the intensified optical image is converted to a digital electronic image using CCD array detectors operated in drift scanning mode.

3. A method according to claim 2 wherein the digital electronic image is manipulated to produce a visual image of the body or portion thereof.

4. A method according to claim 3 wherein the transmitted X-radiation is converted to an optical image by scintillator means.

5. A method according to claim 4 wherein the optical image is intensified by an optical image intensifier in combination with one or more fibre-optic tapers used to convey the optical image.

6. A method according to claim 5 wherein a first series of fibre-optic tapers is used to convey an optical image from the scintillator means to an optical image intensifier which intensifies the image, and a second series of fibre-optic tapers conveys the intensified optical image to a corresponding series of CCD array detectors, operated in drift scanning mode, for conversion to an electronic image, the first and second series of fibre-optic tapers serving also to demagnify the image which they convey.

7. A method according to claim 1 wherein an X-ray source and imaging apparatus are located in opposition to one another on opposite sides of a scanning station, the X-ray source and imaging apparatus are supported by a carrier which is caused to move relative to a stationary body, and the source of X-radiation is caused to emit a fanned beam of X-radiation which is collimated in the direction of relative movement of the carrier.

8. A method according to claim 7 wherein the body is a human body and the carrier is caused to move vertically relative to a standing, stationary human body at the scanning station.

9. A method according to claim 8 wherein the X-ray beam has a sufficiently low intensity for the human body to absorb an equivalent dose of $10 \times 10^{-6}$ sievert or less.

10. A method according to claim 1 wherein the body is caused to move between a stationary X-ray source and opposing imaging apparatus.

11. An apparatus for scanning a body, the apparatus comprising an X-ray source for scanning the body with a beam of X-radiation, a collimator which includes a stack of spaced apart, parallel plates for collimating the beam of X-radiation, means for causing relative linear movement, in a direction transverse to the plates of the collimator, between the body which is to be scanned and the X-ray source, and imaging apparatus which includes means for converting X-radiation transmitted by the body into an optical image, means for intensifying the optical image, means for converting the intensified optical image into an electronic image and means for manipulating the electronic image to produce a scanned image of the body or a portion thereof.

12. Apparatus according to claim 11 comprising CCD array detectors, operated in drift scanning mode, to convert the intensified optical image to a digital electronic image.

13. Apparatus according to claim 12 comprising means for producing a scanned video image of the body or a portion thereof.

14. Apparatus according to claim 13 comprising scintillator means to convert the transmitted X-radiation to an optical image.

15. Apparatus according to claim 14 comprising an optical image intensifier in combination with one or more fibre-optic tapers, used to convey the optical image, to intensify the optical image.

16. Apparatus according to claim 15 comprising a first series of fibre-optic tapers to convey an optical image from the scintillator means to an optical image intensifier which intensifies the image, and a second series of fibre-optic tapers conveys the intensified optical image to a corresponding series of CCD array detectors, operated in drift scanning mode, for conversion to an electronic image, the first and second series of fibre-optic tapers serving also to demagnify the image which they convey.

17. Apparatus according to claim 16 comprising an X-ray source and imaging apparatus which are located in opposition to one another on opposite sides of a scanning station, a carrier supporting the X-ray source and imaging apparatus, and means for causing the carrier to move relative to a stationary body at the scanning station with the source of X-radiation emitting a fanned beam of X-radiation which is collimated in the direction of relative movement of the carrier.

18. Apparatus according to claim 17 comprising an X-ray source in the form of a line-focus X-ray tube orientated in the direction of movement of the carrier relative to the body.

19. Apparatus according to claim 17 when used to scan a human body, the carrier being movable vertically relative to a human body standing at the scanning station.

20. Apparatus according to claim 19 wherein the beam of X-radiation has a sufficiently low intensity for the human body to absorb an equivalent dose of $10 \times 10^{-6}$ sievert or less.

21. Apparatus according to claim 16 comprising a stationary X-ray course and opposing imaging apparatus, and means for moving the body between the X-ray source and imaging apparatus.

* * * * *